United States Patent

Kirstgen et al.

[11] Patent Number: 5,935,965
[45] Date of Patent: Aug. 10, 1999

[54] 2-[(2-ALKOXY-6-TRIFLUOROMETHYLPYRIMIDIN-4-YL) OXYMETHYLENE]PHENYLACETIC ACID DERIVATIVES, THEIR PREPARATION AND INTERMEDIATE THEREFOR, AND USE THEREOF

[75] Inventors: Reinhard Kirstgen, Neustadt; Klaus Oberdorf, Heidelberg; Franz Schütz, Neustadt; Hans Theobald, Limburgerhof; Volker Harries, Frankenthal, all of Germany

[73] Assignee: BASF Aktiengesellschaft, Ludwigshafen, Germany

[21] Appl. No.: 08/836,255

[22] PCT Filed: Nov. 7, 1995

[86] PCT No.: PCT/EP95/04375

§ 371 Date: May 6, 1997

§ 102(e) Date: May 6, 1997

[87] PCT Pub. No.: WO96/16047

PCT Pub. Date: May 30, 1996

[30] Foreign Application Priority Data

Nov. 17, 1994 [DE] Germany .............................. 44 40 930
Jul. 21, 1995 [DE] Germany .......................... 195 26 661

[51] Int. Cl.$^6$ ........................ A61K 31/505; C07D 239/34
[52] U.S. Cl. ......................... 514/274; 544/314; 544/311; 544/312
[58] Field of Search ........................... 514/274; 544/314, 544/311, 312

[56] References Cited

U.S. PATENT DOCUMENTS

| | | | |
|---|---|---|---|
| 4,829,085 | 5/1989 | Wenderoth et al. | 514/522 |
| 4,857,545 | 8/1989 | Anthony et al. | 514/452 |
| 4,877,811 | 10/1989 | Anthony et al. | 514/522 |
| 4,976,771 | 12/1990 | Anthony et al. | 549/16 |
| 4,999,042 | 3/1991 | Anthony et al. | 544/384 |
| 5,021,581 | 6/1991 | Clough et al. | 546/309 |
| 5,047,408 | 9/1991 | Schuetz et al. | 514/274 |
| 5,106,852 | 4/1992 | Schuetz et al. | 514/269 |
| 5,157,037 | 10/1992 | Schuetz et al. | 514/269 |
| 5,157,144 | 10/1992 | Anthony et al. | 560/35 |
| 5,192,357 | 3/1993 | Cliff et al. | 504/315 |
| 5,194,438 | 3/1993 | Schuetz et al. | 514/269 |
| 5,334,577 | 8/1994 | Wenderoth et al. | 504/130 |
| 5,395,854 | 3/1995 | Brand et al. | 514/619 |
| 5,416,068 | 5/1995 | Grammenos et al. | 504/378 |
| 5,468,717 | 11/1995 | Wenderoth et al. | 504/130 |
| 5,516,804 | 5/1996 | Brand et al. | 514/619 |
| 5,523,454 | 6/1996 | Brand et al. | 558/408 |
| 5,554,578 | 9/1996 | Wenderoth et al. | 504/130 |

FOREIGN PATENT DOCUMENTS

| | | |
|---|---|---|
| 178 826 | 4/1986 | European Pat. Off. . |
| 253 213 | 1/1988 | European Pat. Off. . |
| 254 426 | 1/1988 | European Pat. Off. . |
| 278 595 | 8/1988 | European Pat. Off. . |
| 299 694 | 1/1989 | European Pat. Off. . |
| 350 691 | 1/1990 | European Pat. Off. . |
| 363 818 | 4/1990 | European Pat. Off. . |
| 407 873 | 1/1991 | European Pat. Off. . |
| 477 631 | 4/1992 | European Pat. Off. . |
| 513 580 | 11/1992 | European Pat. Off. . |
| 90/05309 | 5/1990 | WIPO . |

OTHER PUBLICATIONS

Lutz et al., "Novel 6–trifluoromethyl cytosines and uracils", *J. of Heterocyclic Chem.*, vol. 9, No. 3, Jun. 1972, pp. 513–521.

*Primary Examiner*—Jane Fan
*Attorney, Agent, or Firm*—Keil & Weinkauf

[57] ABSTRACT

2-[(2-Alkoxy-6-trifluoromethylpyrimidin-4-yl) oxymethylene]-phenylacetic acid derivatives of the formula I

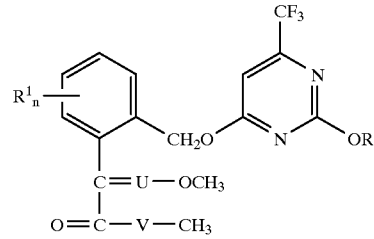

where the index and the substituents have the following meanings:
  U is CH or N;
  V is O or NH;
  R is alkyl;
  $R^1$ is cyano, halogen, alkyl, haloalkyl, alkoxy, haloalkoxy or phenyl;
  n is 0 or an integer from 1 to 4,
processes and intermediates for their preparation, and their use are described.

13 Claims, No Drawings

2-[(2-ALKOXY-6-TRIFLUOROMETHYLPYRIMIDIN-4-YL)OXYMETHYLENE]PHENYLACETIC ACID DERIVATIVES, THEIR PREPARATION AND INTERMEDIATE THEREFOR, AND USE THEREOF

This application is a 371 of PCT/EP95/04375 Nov. 7, 1995 now 96/16047 May 30, 1996.

The present invention relates to 2-[(2-alkoxy-6-trifluoromethyl-pyrimidin-4-yl)oxymethylene]phenylacetic acid derivatives of the formula I

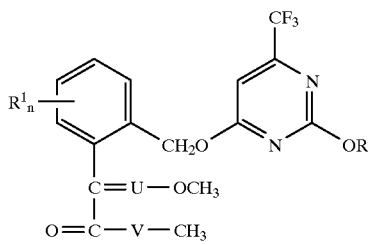

where the index and the substituents have the following meanings:

U is CH or N;
V is O or NH;
R is $C_1$–$C_6$-alkyl;
$R^1$ is cyano, halogen, $C_1$–$C_4$-alkyl, $C_1$–$C_4$-haloalkyl, $C_1$–$C_4$-alkoxy, $C_1$–$C_4$-haloalkoxy or phenyl;
n is 0 or an integer from 1 to 4, it being possible for the radicals $R^1$ to be different if the value of n is greater than 1.

In addition, the invention relates to processes and intermediates for preparing these compounds and to compositions containing them, and their use.

Methyl α-hetaryloxymethylenephenyl-β-methoxyacrylates are described in the literature as fungicides (EP-A 178 826, EP-A 278 595, EP-A 350 691). EP-A 407 873 additionally describes corresponding methyl α-[2-(6-trifluoromethylpyrimidin-4-yl)-oxymethylenephenyl]-β-methoxyacrylates having acaricidal and insecticidal action.

Methyl α-[2-(hetaryloxymethylene)phenyl]-α-methoxyiminoacetates having fungicidal (EP-A 253 213, EP-A 254 426, EP-A 299 694, EP-A 363 818) and insecticidal or acaricidal action (EP-A 407 873) have additionally been disclosed.

In addition, the literature describes α-[2-(hetaryloxymethylene)-phenyl]-α-methoxyimino-N-methylacetamides having fungicidal (EP-A 396 692) and insecticidal or acaricidal action (EP-A 477 631).

The action of the compounds described there against animal pests, however, is unsatisfactory in many cases.

It is an object of the present invention to provide compounds having improved properties in the control of harmful fungi and animal pests, in particular harmful fungi, insects, nematodes and acarids, especially insects and acarids.

We have now found that this object is achieved by the compounds I defined at the outset. In addition, we have found processes and intermediates for their preparation, compositions containing them and methods for their use.

The compounds I are prepared in a similar way to the processes described in the literature mentioned at the outset. The compounds I are obtained here, for example, by reacting a pyrimidin-4-ol of the formula II in a manner known per se in an inert organic solvent in the presence of a base with a benzyl derivative of the formula III.

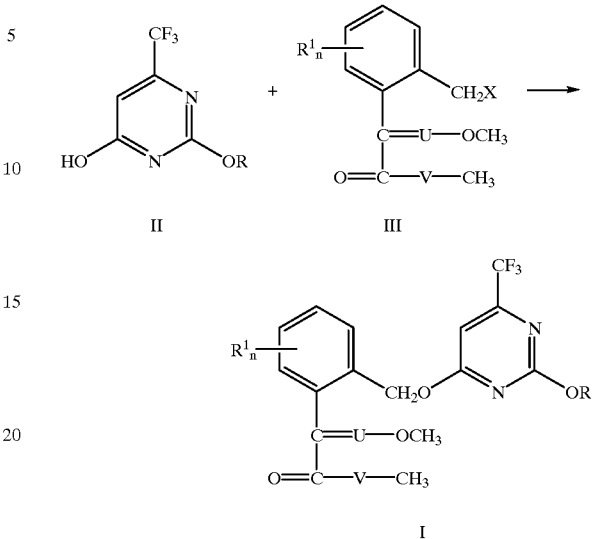

In the formula III, X is a nucleophilically replaceable leaving group such as halogen (eg. chlorine, bromine or iodine) or alkyl- or arylsulfonyl (eg. methylsulfonyl, trifluoromethylsulfonyl, phenylsulfonyl or 4-methylphenylsulfonyl).

This reaction is customarily carried out at from 0° C. to 80° C., preferably 20° C. to 60° C.

Suitable solvents are aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, isopropanol, n-butanol and tert-butanol, ketones such as acetone and methyl ethyl ketone, and also dimethyl sulfoxide, dimethylformamide, dimethylacetamide, 1,3-dimethylimidazolidin-2-one and 1,3-dimethyltetrahydro-2(1H)-pyrimidinone, particularly preferably methylene chloride, acetone and dimethylformamide.

Mixtures of the solvents mentioned can also be used.

Suitable bases are generally inorganic compounds such as alkali metal and alkaline earth metal hydroxides such as lithium hydroxide, sodium hydroxide, potassium hydroxide, calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as potassium carbonate and calcium carbonate and also alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride and also alkali metal and alkaline earth metal alkoxides such as sodium methoxide, sodium ethoxide, potassium ethoxide, potassium tert-butoxide and dimethoxymagnesium, additionally organic bases, eg. tertiary amines such as trimethylamine, triethylamine, diisopropylethylamine and N-methylpiperidine, pyridine, substituted pyridines such as collidine, lutidine and 4-dimethylaminopyridine and also bicyclic amines.

Sodium hydroxide, sodium hydride, potassium carbonate and potassium tert-butoxide are particularly preferred.

The bases are in general used in an equimolar amount, in an excess or if appropriate as a solvent.

It may be advantageous for the reaction to add a catalytic amount of a crown-ether such as eg. 18-crown-6 or 15-crown-5.

The reaction can also be carried out in two-phase systems consisting of a solution of alkali metal or alkaline earth metal hydroxides or alkali metal or alkaline earth metal carbonates in water and an organic phase such as eg. halogenated hydrocarbons. The phase-transfer catalysts employed can be ammonium halides and tetrafluoroborates such as eg. benzyltriethylammonium chloride, benzyltributylammonium bromide, tetrabutylammonium chloride, hexadecyltrimethylammonium bromide or tetrabutylammonium tetrafluoroborate and also phosphonium halides such as tetrabutylphosphonium chloride or tetraphenylphosphonium bromide.

It may be advantageous for the reaction first to treat the compounds II with base and to react the resulting salt with the compounds III.

The compounds II can be obtained by condensation of trifluoroacetic acid esters VI with O-alkylisoureas VII in a similar manner to known processes [cf. J. Chem. Soc 1946, 5].

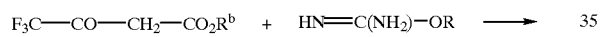

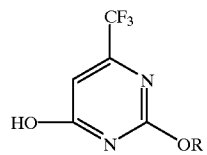

$R^b$ in the formula VI is a $C_1$–$C_4$-alkyl group, in particular methyl or ethyl.

The reaction is customarily carried out at from 0° C. to 120° C., preferably 20° C. to 80° C., in particular at the boiling point of the solvent. Solvents used are customarily alcohols, in particular methanol or ethanol.

The O-alkylisoureas of the formula VII are customarily employed in the form of their salts, in particular as hydrohalides (eg. hydrochloride and hydrobromide). When using salts, it is recommended to carry out the reaction in the presence of a base (eg. alkaline earth metal or alkali metal alkoxides or hydroxides such as sodium methoxide, sodium ethoxide, potassium tert-butoxide, sodium hydroxide, potassium hydroxide or calcium hydroxide).

Alternatively, the compounds I are also obtained by reacting a sulfone derivatiwe of the formula IV in a manner known per se [cf. J. Med. Chem. 27 (1984), 1621; CH-A 649 068] in the presence of a base with an alcohol of the formula V.

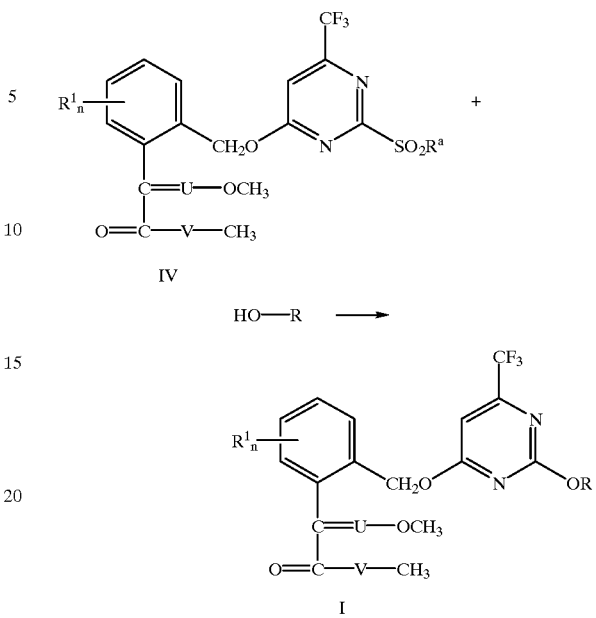

$R^a$ in the formula IV is $C_1$–$C_4$-alkyl, in particular methyl.

Suitable bases are, in particular, sodium hydride, potassium tert-butoxide and potassium carbonate.

The reaction is in general carried out in an inert dipolar aprotic solvent (in particular dimethyl sulfoxide, dimethylformamide or 1,3-dimethyltetrahydro-2(1H)-pyrimidinone).

The sulfone derivatives of the formula IV needed for the reaction are obtained starting from corresponding sulfides VIII by oxidation.

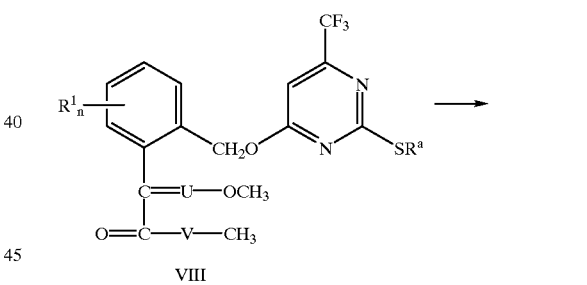

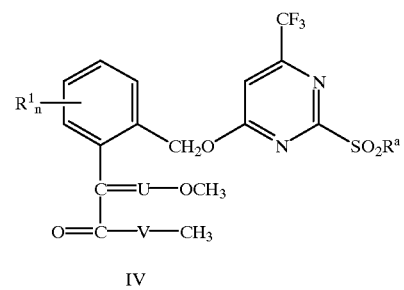

The oxidation is carried out according to the processes known from the literature, for example using hydrogen peroxide in concentrated acetic acid [cf. Chem. Pharm. Bull. 27 (1978), 183] or using sodium hypochlorite in water [cf. J. Prakt. Chem. 33 (1966), 165].

The benzyl derivatives of the formula III where V is oxygen are known from the literature cited at the outset. Benzyl derivatives II where U is N and V is NH are described in DE-A 43 05 502.

Alternatively, the compounds of the general formula I where U is N and V is NH are obtained by aminolysis of the corresponding esters (V=O) (cf. Houben-Weyl Vol. E5, p. 983 ff.).

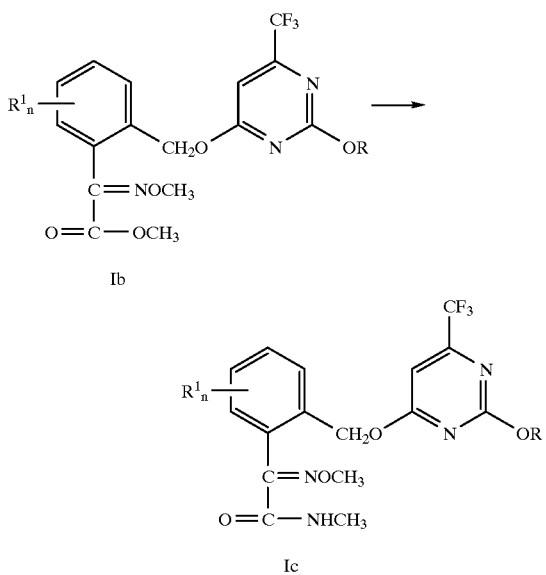

Ib

Ic

This reaction is customarily carried out at from 0° C. to 60° C., preferably 10° C. to 30° C., in an inert solvent.

Methylamine can be introduced as a gas or metered in as an aqueous solution.

Suitable solvents are aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, tetrahydrofuran and anisole, alcohols such as methanol, ethanol, n-propanol, isopropanol, n-butanol and tert-butanol, particularly preferably methanol, toluene and tetrahydrofuran. Mixtures of the solvents mentioned can also be used.

In the definitions of the symbols indicated in the above formulae, collective terms were used which are generally representative of the following substituents:

Halogen: fluorine, chlorine, bromine and iodine;

Alkyl: saturated, straight-chain or branched hydrocarbon radicals having 1 to 6 carbon atoms such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methyl-pentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-l-methylpropyl and 1-ethyl-2-methylpropyl;

Haloalkyl: straight-chain or branched alkyl groups having 1 to 4 carbon atoms (as mentioned above), it being possible in these groups for the hydrogen atoms to be partly or completely replaced by halogen atoms as mentioned above, eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 4 carbon atoms (as mentioned above), which are bonded to the structure via an oxygen atom (-o-);

Haloalkoxy.- straight-chain or branched haloalkyl groups having 1 to 4 carbon atoms (as mentioned above) which are bonded to the structure via an oxygen atom (-o-).

With respect to their biological activity, those compounds I are particularly preferred in which R is $C_2$–$C_5$-alkyl, in particular $C_2$–$C_4$-alkyl.

Compounds I are additionally preferred in which n is 0 or 1, in particular 0.

In the case where n is not 0, compounds I are preferred in which $R^1$ has the following meaning: cyano, fluorine, chlorine, methyl, trifluoromethyl or methoxy.

Compounds I are additionally preferred in which one radical $R^1$ is bonded in the 3-, 4- or 5-position of the phenyl ring.

In particular, with respect to their use, the compounds I compiled in the following table are preferred. The groups mentioned in the table for a substituent are additionally considered per se (independently of the combination in which they are mentioned) to be a particularly preferred embodiment of the substituent concerned.

Table 1

Compounds of the formula I where U is CH and V is O. (≡Ia) and the combination of the substituents $R^1_n$ and R for a compound corresponds to one line of Table A.

Table 2

Compounds of the formula I where U is N and V is O (≡Ib) and the combination of the substituents $R^1_n$ and R for a compound corresponds to one line of Table A.

Table 3

Compounds of the formula I where U is N and V is NH (≡Ic) and the combination of the substituents $R^1_n$ and R for a compound corresponds to one line of Table A.

TABLE A

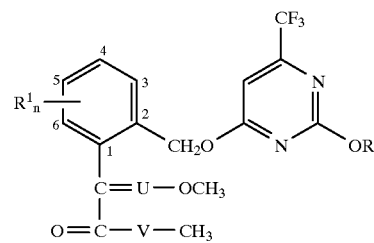

| No. | $R^1_n$ | R |
|---|---|---|
| 01 | H | $CH_3$ |
| 02 | H | $CH_2CH_3$ |
| 03 | 3-Cl | $CH_2CH_3$ |
| 04 | 4-$OCH_3$ | $CH_2CH_3$ |
| 05 | H | $CH_2CH_2CH_3$ |
| 06 | 3-Cl | $CH_2CH_2CH_3$ |
| 07 | H | $CH(CH_3)_2$ |
| 08 | 3-Cl | $CH(CH_3)_2$ |
| 09 | 4-OCH | $CH(CH_3)_2$ |
| 10 | 5-$C(CH_3)_3$ | $CH(CH_3)_2$ |
| 11 | H | $CH_2CH_2CH_2CH_3$ |
| 12 | H | $CH_2CH(CH_3)_2$ |
| 13 | H | $CH(CH_3)CH_2CH_3$ |

The compounds of the formula I according to the invention are suitable for controlling animal pests of the insects, acarids and nematodes class, in particular insects, especially acarids. They can be employed as fungicides and pesticides in crop protection and in the hygiene, stored material protection and veterinary sectors.

The harmful insects include:

from the order of the butterflies (Lepidoptera), for example, *Adoxophyes orana, Agrotis ypsilon, Agrotis segetum, Alabama argillacea, Anticarsia gemmatalis, Argyresthia conjugella, Autographa gamma, Cacoecia murinana, Capua reticulana, Choristoneura fumiferana, Chilo partellus, Choristoneura occidentalis, Cirphis unipuncta, Cnaphalocrocis medinalis, Crocidolomia binotalis, Cydia pomonella, Dendrolimus pini, Diaphania nitidalis, Diatraea grandiosella, Earias insulana, Elasmopalpus lignosellus, Eupoecilia ambiguella, Feltia subterranea, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera scitella, Lithocolletis blancardella, Lobesia botrana, Loxostege sticticalis, Lymantria dispar, Lymantria monacha, Lyonetia clerkella, Manduca sexta, Malacosoma neustria, Mamestra brassicae, Mocis repanda, Operophthera brumata, Orgyia pseudotsugata, Ostrinia nubilalis, Pandemis heparana, Panolis flammea, Pectinophora gossypiella, Phthorimaea operculella, Phyllocnistis citrella, Pieris brassicae, Plathypena scabra, Platynota stultana, Plutella xylostella, Prays citri, Prays oleae, Prodenia sunia, Prodenia ornithogalli, Pseudoplusia includens, Rhyacionia frustrana, Scrobipalpula absoluta, Sesamia inferens, Sparganothis pilleriana, Spodoptera frugiperda, Spodoptera littoralis, Spodoptera litura, Syllepta derogata, Synanthedon myopaeformis, Thaumatopoea pityocampa, Tortrix viridana, Trichoplusia ni, Tryporyza incertulas, Zeiraphera canadensis,* also *Galleria mellonella* and *Sitotroga cerealella, Ephestia cautella, Tineola bisselliella*;

from the order of the beetles (Coleoptera), for example, *Agriotes lineatus, Agriotes obscurus, Anthonomus grandis, Anthonomus pomorum, Apion vorax, Atomaria linearis, Blastophagus piniperda, Cassida nebulosa, Cerotoma trifurcata, Ceuthorhynchus assimilis, Ceuthorhynchus napi, Chaetocnema tibialis, Conoderus vespertinus, Crioceris asparagi, Dendroctonus refipennis, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllopertha horticola,* Phyllophaga sp., *Phyllotreta chrysocephala, Phyllotreta nemorum, Phyllotreta striolata, Popillia japonica, Psylliodes napi, Scolytus intricatus, Sitona lineatus,* also *Bruchus rufimanus, Bruchus pisorum, Bruchus lentis, Sitophilus granaria, Lasioderma serricorne, Oryzaephilus surinamensis, Rhyzopertha dominica, Sitophilus oryzae, Tribolium castaneum, Trogoderma granarium, Zabrotes subfasciatus*;

from the order of the dipterous insects (Diptera), for example, *Anastrepha ludens, Ceratitis capitata, Contarinia sorghicola, Dacus cucurbitae, Dacus oleae, Dasineura brassicae, Delia coarctata, Delia radicum, Hydrellia griseola, Hylemyia platura, Liriomyzasativae, Liriomyza trifolii, Mayetiola destructor, Orseolia oryzae, Oscinella frit, Pegomya hyoscyami, Phorbia antiqua, Phorbia brassicae, Phorbia coarctata, Rhagoletis cerasi, Rhagoletis pomonella, Tipula oleracea, Tipula paludosa,* also *Aedes aegypti, Aedes vexans, Anopheles maculipennis, Chrysomya bezziana, Chrysomya hominivorax, Chrysomya macellaria, Cordylobia anthropophaga, Culex pipiens, Fannia canicularis, Gasterophilus intestinalis, Glossina morsitans, Haematobia irritans, Haplodiplosis equestris, Hypoderma lineata, Lucilia caprina, Lucilia cuprina, Lucilia sericata, Musca domestica, Muscina stabulans, Oestrus ovis, Tabanus bovinus, Simulium damnosum*;

from the order of the thrips (Thysanoptera), for example, *Frankliniella fusca, Frankliniella occidentalis, Frankliniella tritici, Haplothrips tritici, Scirtothrips citri, Thrips oryzae, Thrips palmi, Thrips tabaci*;

from the order of the hymenopterous insects (Hymenoptera), for example, *Athalia rosae, Atta cephalotes, Atta sexdens, Atta texana, Hoplocampa minuta, Hoplocampa testudinea, Iridomyrmes humilis, Iridomyrmex purpureus, Monomorium pharaonis, Solenopsis geminata, Solenopsis invicta, Solenopsis richteri*;

from the order of the bugs (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus hesperus, Lygus lineolaris, Lygus pratensis, Nezara viridula, Piesma quadrata, Solubea insularis, Thyanta perditor*;

from the order of the plant-sucking insects (Homoptera), for example, Acyrthosiphon onobrychis, *Acyrthosiphon pisum, Adelges laricis, Aonidiella aurantii, Aphidula nasturtii, Aphis fabae, Aphis gossypii, Aphis pomi, Aulacorthum solani, Bemisia tabaci, Brachycaudus cardui, Brevicoryne brassicae, Dalbulus maidis, Dreyfusia nordmannianae, Dreyfusia piceae, Dysaphis radicola, Empoasca fabae, Eriosoma lanigerum, Laodelphax striatella, Macrosiphum avenae, Macrosiphum euphorbiae, Macrosiphon rosae, Megoura viciae, Metopolophium dirhodum, Myzus persicae, Myzus cerasi, Nephotettix cincticeps, Nilaparvata lugens, Perkinsiella saccharicida, Phorodon humuli, Planococcus citri, Psylla mali, Psylla piri, Psylla pyricol, Quadraspidiotus perniciosus, Rhopalosiphum maidis, Saissetia oleae, Schizaphis graminum, Selenaspidus articulatus, Sitobion avenae, Sogatella furcifera, Toxoptera citricida, Trialeurodes abutilonea, Trialeurodes vaporariorum, Viteus vitifolii*;

from the order of the termites (Isoptera), for example, *Calotermes flavicollis, Leucotermes flavipes, Macrotermes subhyalinus, Odontotermes formosanus, Reticulitermes lucifugus, Termes natalensis*;

from the order of the orthopterous insects (Orthoptera), for example, *Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca peregrina, Stauronotus maroccanus, Schistocerca gregaria,* also *Acheta domestica, Blatta orientalis, Blattella germanica, Periplaneta americana*;

from the order of the Arachnoidea, for example, *phytophagous mites such as Aculops lycopersicae, Aculops pelekassi, Aculus schlechtendali, Brevipalpus phoenicis, Bryobia praetiosa, Eotetranychus carpini, Eutetranychus banksii, Eriophyes sheldoni, Oligonychus pratensis, Panonychus ulmi, Panonychus citri, Phyllocoptruta oleivora, Polyphagotarsonemus latus, Tarsonemus pallidus, Tetranychus cinnabarinus, Tetranychus kanzawai, Tetranychus pacificus, Tetranychus urticae,* ticks such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Rhipicephalus appendiculatus and Rhipicephalus evertsi* and *animal-parasitic mites* such as *Dermanyssus gallinae, Psoroptes ovis* and *Sarcoptes scabiei*;

from the class of the nematodes, for example, root gall nematodes, eg. *Meloidogyne hapla, Meloidogyne incognita, Meloidogyne javanica,* cyst-forming nematodes, eg. *Globodera pallida, Globodera rostochiensis, Heterodera avenae, Heterodera glycines, Heterodera schachtii,* migratory endoparasites and semi-endoparasitic nematodes, eg. *Heliocotylenchus multicinctus, Hirschmanniella oryzae,* Hoplolaimus spp., *Pratylenchus brachyurus, Pratylenchus fallax, Pratylenchus penetrans, Pratylenchus vulnus, Radopholus similis, Rotylenchus reniformis, Scutellonema bradys, Tylenchulus semipenetrans,* stem and leaf nematodes, eg. *Anguina tritici, Aphelenchoides besseyi, Ditylenchus angustus, Ditylenchus dipsaci,* virus vectors, eg. Longidorus spp., *Trichodorus christei, Trichodorus viruliferus, Xiphinema index, Xiphinema mediterraneum.*

The compounds I are additionally suitable as fungicides.

The compounds I are distinguished by an outstanding activity against a wide spectrum of phytopathogenic fungi, in particular from the Ascomycetes and Basidiomycetes classes. In some cases they are systemically active and can be employed as foliar and soil fungicides.

They are particularly important for the control of a multiplicity of fungi on various crop plants such as wheat, rye, barley, oats, rice, corn, grass, cotton, soybeans, coffee, sugar cane, vines, fruit plants and decorative plants and vegetable plants such as cucumbers, beans and cucurbits, and on the seeds of these plants.

They are especially suitable for the control of the following plant diseases: *Erysiphe graminis* (powdery mildew) in cereals, *Erysiphe cichoracearum* and *Sphaerotheca fuliginea* on cucurbits, *Podosphaera leucotricha* on apples, *Uncinula necator* on vines, Puccinia specieson cereals, Rhizoctonia species on cotton and grass, Ustilago species on cereals and sugar cane, *Venturia inaequalis* (scab) on apples, Helminthosporium species on cereals, *Septoria nodorum* on wheat, *Botrytis cinerea* (grey mold) on strawberries and vines, *Cercospora arachidicola* on groundnuts, *Pseudocercosporella herpotrichoides* on wheat and barley, *Pyricularia oryzae* on rice, *Phytophthora infestans* on potatoes and tomatoes, Fusarium and Verticillium species on various plants, *Plasmopara viticola* on vines, and Alternaria species on vegetables and fruit.

The compounds I are applied by treating the fungi or the plants, seeds, materials or the ground to be protected from fungal attack with a fungicidally active amount of the active compounds. Application is carried out before or after the infection of the materials, plants or seeds by the fungi.

They can be converted into the customary formulations, such as solutions, emulsions, suspensions, dusts, powders, pastes and granules. The application form depends on the particular intended use; in each case it should guarantee a fine and uniform dispersion of the 2-[(2-alkoxy-6-trifluoromethylpyrimidin-4-yl)-oxymethylene]phenylacetic acid derivatives. The formulations are prepared in a known manner, eg. by extending the active compound using solvents and/or carriers, if desired using emulsifiers and dispersants, it also being possible if water is used as a diluent to use other organic solvents as auxiliary solvents. Suitable auxiliaries for this purpose are essentially: solvents such as aromatics (eg. xylene), chlorinated aromatics (eg. chlorobenzenes), paraffins (eg. petroleum fractions), alcohols (eg. methanol, butanol), ketones (eg. cyclohexanone), amines (eg. ethanolamine, dimethylformamide) and water; carriers such as ground natural minerals (eg. kaolins, aluminas, talc, chalk) and ground synthetic minerals (eg. highly disperse silicic acid, silicates); emulsifiers such as nonionic and anionic emulsifiers (eg. polyoxyethylene fatty alcohol ethers, alkylsulfonates and arylsulfonates) and dispersants such as lignin-sulfite waste liquors and methylcellulose.

The fungicidal compositions in general contain from 0.1 to 95, preferably from 0.5 to 90, % by weight of active compound.

Depending on the effect desired, the application rates are from 0.01 to 2.0 kg of active compound per ha.

In the treatment of seed, amounts of active compound of from 0.001 to 0.1 g, preferably 0.01 to 0.05 g, per kilogram of seed are generally needed.

The active compounds can be used as such, in the form of their formulations or the use forms prepared therefrom by spraying, atomizing, dusting, broadcasting or watering, eg. in the form of directly sprayable solutions, powders, suspensions or dispersions, emulsions, oil dispersions, pastes, dusting compositions, broadcasting compositions or granules. The use forms depend entirely on the intended uses; in each case they should if possible guarantee the finest dispersion of the active compounds according to the invention.

They can be converted into the customary formulations, such as solutions, emulsions, suspensions, dusts, powders, pastes or granules. The use forms here depend on the particular intended use; in each case they should if possible guarantee the finest dispersion of the active compounds.

The formulations are prepared in a known manner, eg. by extending the active compound with solvents and/or carriers, if desired using emulsifiers and dispersants, and if water is used as a diluent other organic solvents can also be used as auxiliary solents.

Suitable auxiliaries for this purpose are mainly:

solvents such as aromatics (eg. xylene), chlorinated aromatics (eg. chlorobenzenes), paraffins (eg. petroleum fractions), alcohols (eg. methanol, butanol), ketones (eg. cyclohexanone), amines (eg. ethanolamine), dimethylformamide and water;

carriers such as ground natural minerals (eg. kaolins, aluminas, talc, chalk) and ground synthetic minerals (eg. highly disperse silica, silicates), emulsifiers such as nonionic and anionic emulsifiers (eg. polyoxyethylene fatty alcohol ethers, alkylsulfonates and arylsulfonates) and dispersants such as lignin-sulfite waste liquors and methylcellulose.

Suitable surface-active substances are the alkali metal, alkaline earth metal and ammonium salts of aromatic sulfonic acids, eg. lignosulfonic, phenolsulfonic, naphthalenesulfonic and dibutylnaphthalenesulfonic acid, and also of fatty acids, alkyl- and alkylarylsulfonates, alkyl, lauryl ether and fatty alcohol sulfates, as well as salts of sulfated hexa-, hepta- and octadecanols, and also of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenol ether, ethoxylated isooctyl-, octyl- or nonylphenol, alkylphenol or tributylphenylpolyglycol ethers, alkylaryl polyether alcohols, isotridecyl alcohol, fatty alcohol ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Aqueous use forms can be prepared from emulsion concentrates, dispersions, pastes, wettable powders or water-dispersible granules by addition of water. To prepare emulsions, pastes or oil dispersions, the substances can be homogenized in water as such or dissolved in an oil or solvent, by means of wetting agents, adhesives, dispersants or emulsifiers. However, concentrates consisting of active substance, wetting agent, adhesive, dispersant or emulsifier and possibly solvent or oil can also be prepared which are suitable for dilution with water.

Powder, scattering and dusting compositions can be prepared by mixing or joint grinding of the active substances with a solid carrier.

Granules, eg. coated, impregnated and homogeneous granules, can be prepared by binding the active compounds to solid carriers.

Solid carriers are mineral earths such as silica gel, silicic acids, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products, such as cereal flour, tree bark meal, wood meal and nutshell meal, cellulose powder or other solid carriers. The active compound concentrations in the ready-to-use preparations can be varied within relatively wide ranges.

Very generally, the compositions contain from 0.0001 to 95% by weight of active compound.

Formulations containing more than 95% by weight of active compound can be applied highly successfully in the ultra-low volume process (ULV), it even being possible to use the active compound without additives.

For use against animal pests, formulations containing from 0.0001 to 10% by weight, preferably from 0.01 to 1% by weight of active compound, are suitable.

The active compounds are normally employed in a purity of from 90% to 100%, preferably from 95% to 100% (according to NMR spectrum).

Examples of such preparations are:

I. a solution of 90 parts by weight of a compound I according to the invention and 10 parts by weight of N-methyl-α-pyrrolidone, which is suitable for application in the form of very small drops;

II. a solution of 20 parts by weight of a compound I according to the invention in a mixture of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid, 5 parts by weight of the addition product of 40 mol of ethylene oxide to 1 mol of castor oil; a dispersion is obtained by finely dispersing the formulation in water.

III. a solution of 20 parts by weight of a compound I according to the invention in a mixture of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil; a dispersion is obtained by finely dispersing the formulation in water.

IV. an aqueous dispersion of 20 parts by weight of a compound I according to the invention in a mixture of 25 parts by weight of cyclohexanone, 65 parts by weight of a petroleum fraction of boiling point from 210 to 280° C. and 10 parts by weight of the addition product of 40 mol of ethylene oxide to 1 mol of castor oil; a dispersion is obtained by finely dispersing the formulation in water.

V. a mixture, ground in a hammer mill, of 20 parts by weight of a compound I according to the invention, 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel; a spray liquor is obtained by finely dispersing the mixture in water;

VI. an intimate mixture of 3 parts by weight of a compound I according to the invention and 97 parts by weight of finely divided kaolin; this dusting composition contains 3% by weight of active compound;

VII. an intimate mixture of 30 parts by weight of a compound I according to the invention, 92 parts by weight of powdered silica gel and 8 parts by weight of liquid paraffin which has been sprayed onto the surface of this silica gel; this preparation gives the active compound a good adhesion;

VIII. a stable aqueous dispersion of 40 parts by weight of a compound I according to the invention, 10 parts by weight of the sodium salt of a phenolsulfonic acid/urea/formaldehyde condensate, 2 parts by weight of silica gel and 48 parts by weight of water, which can be further diluted;

IX. a stable oily dispersion of 20 parts by weight of a compound I according to the invention, 2 parts by weight of the calcium salt of dodecylbenzenesulfonic acid, 8 parts by weight of fatty alcohol polyglycol ether, 2 parts by weight of the sodium salt of a phenolsulfonic acid/urea/formaldehyde condensate and 68 parts by weight of a paraffinic mineral oil;

X. a mixture, ground in a hammer mill, of 10 parts by weight of a compound I according to the invention, 4 parts by weight of the sodium salt of diisobutylnaphthalene-α-sulfonic acid, 20 parts by weight of the sodium salt of a lignosulfonic acid from a sulfite waste liquor, 38 parts by weight of silica gel and 38 parts by weight of kaolin. By finely dispersing the mixture in 10,000 parts by weight of water, a spray mixture is obtained which contains 0.1% by weight of the active compound.

The compounds I are applied by treating the pests or harmful fungi or the seeds, plants, materials or the ground to be protected from pests or harmful fungi with an active amount of the active compounds.

They are applied before or after the infection of the materials, plants or seeds by the harmful fungi.

Depending on the type of effect desired, the application rates are from 0.02 to 3 kg of active compound per ha, preferably from 0.1 to 1 kg/ha.

In seed treatment, amounts of active compound of from 0.001 to 50 g, preferably from 0.01 to 10 g, per kilogram of seed are in general needed.

The application rate of active compound for controlling pests or harmful fungi under outdoor conditions is from 0.02 to 10, preferably from 0.1 to 2.0 kg/ha of active compound.

The compounds I, on their own or in combination with herbicides or fungicides, can also be applied jointly mixed with further crop protection agents, for example with growth regulators or with agents for controlling pests or bacteria. Of interest is also the miscibility with fertilizers or with mineral salt solutions which are employed for eliminating nutritional and trace element deficiencies.

The crop protection agents and fertilizers can be added to the compositions according to the invention in a weight ratio of from 1:10 to 10:1, if appropriate even immediately before use (tank mix). On mixing with fungicides or insecticides, in many cases an increase in the fungicidal spectrum of action is obtained here.

The following list of fungicides with which the compounds according to the-invention can be applied together is intended to illustrate the combination possibilities, but not restrict them:

sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc N,N-ethylenebisdithiocarbamate, ammonia complex of zinc N,N'-propylenebisdithiocarbamate, zinc N,N'-propylenebisdithiocarbamate, N,N'-polypropylenebis (thiocarbamoyl) disulfide; nitro derivatives, such as dinitro(1-methylheptyl)phenyl crotonate, 2-sec-butyl-4,6-dinitrophenyl 3,3-dimethylacrylate, 2-sec-butyl-4, 6-dinitrophenyl isopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-β-[bis-(dimethylamino)-phosphinyl]-3-phenyl-1,2,4-triazole, 2,3-dicyano-1,4-dithioanthraquinone, 2-thio-1,3-dithiolo-β-[4,5-b]quinoxaline, methyl 1-(butylcarbamoyl)-2-benzimidazolecarbamate, 2-methoxycarbonylaminobenzimidazole, 2-(fur-2-yl) benzimidazole, 2-(thiazol-4-yl)benzimidazole, N-(1,1, 2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine 1-oxide, 8-hydroxyguinoline or its copper salt, 2,3-dihydro-5-arboxanilido-6-methyl-1,4-oxathiin, 2,3-dihydro-5-carboxanilido-6-methyl-1,4-oxathiin 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis(l-(2,2,2-trichloroethyl))formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-tri-azol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyr-idinemethanol, 1,2-bis(3-ethoxycarbonyl-2-thioureido)benzene, 1,2-bis(3-methoxycarbonyl-2-thioureido)benzene, and also various fungicides, such as dodecylguanidine acetate, 3-[3-(3, 5-dimethyl-2-oxycyclohexyl)-2-hydroxyethyl]glutarimide, hexachlorobenzene, DL-methyl N-(2,6-dimethylphenyl)-N-2-furoylalaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichloro-phenyl)-5-methyl-5-methoxymethyl-1, 3-oxazolidine-2,4-dione, 3-(3,5-dichloro-phenyl)-1-isopropylcarbamoylhydantoin, N-(3,5-dichlorophenyl)-1,2-dimethylcyclopropane-1,2-dicarbox-imide, 2-cyano-N-ethylaminocarbonyl-2-methoximinoacetamide, 1-[2-(2,4-dichlorophenyl) pentyl]-1H-1,2,4-triazole, 2,4-difluoro-α-(1H-1,2,4-triazo-1yl-1-methyl)benzhydryl alcohol, N-(3-chloro-2,6-dinitro-4-tri-fluoromethylphenyl)-5-trifluoromethyl-3-chloro-2-aminopyridine, 1-((bis(4-fluorophenyl)methyl-silyl)methyl)-1H-1,2,4-triazole.

SYNTHESIS EXAMPLES

The procedures presented in the Synthesis Examples below were used with appropriate modification of the starting compounds or intermediates to obtain further compounds I. The compounds thus obtained are listed with physical data in the following Tables.

Example 1

2-Isopropoxy-6-trifluoromethyl-4-hydroxypyrimidine 465 g of 30% strength methanolic sodium methoxide solution are added dropwise at room temperature to 357.8 g of o-isopropylisourea hydrochloride (or o-isopropyluronium chloride) in 906 ml of absolute ethanol. After a further 10 min, 475.2 g of ethyl trifluoroacetoacetate are added dropwise to this mixture with a slightly exothermic reaction. After heating under reflux for 12 h, the mixture is concentrated in a rotary evaporator and the residue is taken up in 1 liter of water. The aqueous phase is rendered weakly acidic with hydrochloric acid and then extracted with methyl tert-butyl ether. The combined ether phases are washed with water, dried over sodium sulfate and finally concentrated to dryness. The residue is stirred with petroleum ether, filtered off with suction and dried.

294.5 g of the title compound are obtained as colorless crystals.

M.p. 126–127° C.

$^1$H-NMR (CDC$_3$, δ in ppm):

1.4 (6H); 5.9 (1H); 6.5 (1H); 12.2 (1H)

Example 2

Methyl 3-methoxy-2-[2-(2-methylsulfonyl-6-trifluoromethylpyrimidin-4-yloxymethyl)phenyl]acrylate (Tab. I.04)

0.15 g of disodium tungstate·2H$_2$O is added to a suspension of 3.9 g of methyl 3-methoxy-2-[2-(2-methylthio-6-trifluoromethylpyrimidin-4-yloxymethyl)phenyl]acrylate in 19 ml of glacial acetic acid, and 2.8 ml of 30% strength aqueous H$_2$O solution are slowly added dropwise at 20–30° C. The mixture clears within 1 h and is stirred at room temperature for a further 12 h. For working up, it is poured onto 100 ml of ice water, the supernatant is decanted off after about 30 min and the remaining viscous solid is taken up in ethyl acetate. This organic phase is washed with water, dried over sodium sulfate and finally concentrated. 4.0 g of the title compound remain as a pale yellow oil.

$^1$H-NMR (CDCl$_3$, δ in ppm):

3.3 (3H); 3.65 (3H); 3.85 (3H); 5.5 (2H); 7.15 (1H); 7.2 (1H); 7.4 (2H); 7.55 (1H); 7.6 (1H)

TABLE 2

II

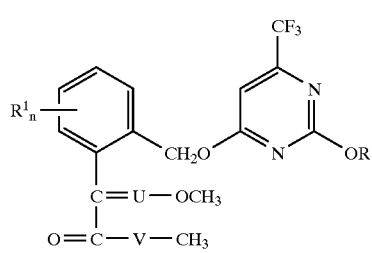

| No. | R | M.p. [° C.] |
|---|---|---|
| II.01 | CH$_3$ | 142–143 |
| II.02 | CH$_2$CH$_3$ | 102–106 |
| II.03 | CH(CH$_3$)$_2$ | 118–120 |

Example 3

Methyl 3-methoxy-2-[2-(2-isopropoxy-6-trifluoromethylpyrimidin-4-yloxymethyl)phenyl]acrylate (I.03)

To prepare the potassium salt of the hydroxypyrimidine from Example 1, 222 g of hydroxy compound are dissolved in 855 ml of ethanol and added dropwise to a solution of 56 g of potassium hydroxide in 855 ml of ethanol. After heating under reflux for 3 hours, the mixture is concentrated and the residue is taken up in 2 l of N,N-dimethylformamide. 280 g of methyl 3-methoxy-2-[2-bromomethylphenyl]acrylate are added to this solution of the potassium salt and it is then stirred at 60° C. for 12 h. For working up, it is poured onto ice water and extracted again with methyl tert-butyl ether. The combined ether phases are washed with water, dried over sodium sulfate and finally concentrated. To remove an N-alkylated by-product, the residue is dissolved in 1 liter of methanol and treated with 250 ml of water. The crystalline precipitate is filtered off with suction, washed with petroleum ether and dried. 211 g of the title compound are obtained.

M.p. 107° C.

$^1$H-NMR (CDCl$_3$, δ in ppm):

1.4 (6H); 3.7 (3H); 3.8 (3H); 5.3 (1H); 5.35 (2H); 6.65 (1H);, 7.2 (1H); 7.4 (2H); 7.5 (1H); 7.55 (1H)

Example 4

Methyl 2-methoxyimino-2-[3-chloro-2-(2-isopropoxy-6-trifluoromethylpyrimidin-4-yloxymethyl)phenyl]acetate (I.08)

3.3 g of 2-isopropoxy-4-hydroxy-6-trifluoromethylpyrimidine and 2.4 g of potassium carbonate are stirred at room temperature (about 25° C.) for 30 min in 100 ml of dimethyl formamide and the mixture is then treated dropwise in the course of 1 hour with a solution of 4.8 g of methyl 2-methoxyimino-2-[2-bromomethyl-3-chlorophenyl]acetate in 30 ml of dimethylformamide. After a further 8 hours at room temperature, the reaction mixture is added to ice water and the product is extracted using tert-butyl methyl ether. The combined ether phases are dried and concentrated. The crude product thus obtained is purified by chromatography (silica gel/toluene). 4.2 g of the title compound are obtained.

M.p. 106–108° C.

$^1$H-NMR (CDCl$_3$, δ in ppm):

1.4 (6H); 3.85 (3H); 4.0 (3H); 5.35 (1H); 5.45 (1H); 6.6 (1H); 7.1 (1H); 7.4 (1H); 7.55 (1H)

Example 5

2-Methoxyimino-2-[3-chloro-2-(2-isopropoxy-6-trifluoromethyl-pyrimidin-4-yloxymethyl)phenyl]-N-methylacetamide (I.11)

A mixture of 2.0 g of the methyl ester from Example 4 and 70 ml of tetrahydrofuran are treated with 2 ml of a 40% strength aqueous methylamine solution. After 8 hours at room temperature (about 25° C.) 100 ml of tert-butyl methyl ether are added to the reaction mixture. The mixture thus obtained is washed 3 times with 20% strength citric acid and twice with water. The organic phase is dried and concentrated. The crude product thus obtained is purified by chromatography [silica gel/toluene: ethyl acetate (9:1)]. 1.0 g of the title compound is obtained.

M.p. 116–118° C.

$^1$H-NMR (CDCl$_3$, δ in ppm):

1.4 (6H); 2.95 (3H); 3.9 (3H); 5.35 (1H); 5.45 (1H); 6.6 (1H); 6.8 (NH); 7.1 (1H); 7.35 (1H); 7.5 (1H)

TABLE I

I

| No. | U | V | R$^1_n$ | R | Phys. data [M.p. (° C.), IR (cm$^{-1}$), $^1$H-NMR (ppm)] |
|---|---|---|---|---|---|
| I.01 | CH | O | H | CH$_3$ | 3.65(3H); 3.75(3H); 4.0 (3H); 5.4(2H); 6.65(1H); 7.1–7.6(5H) |
| I.02 | CH | O | H | CH$_2$CH$_3$ | 66–68 |
| I.03 | CH | O | H | CH(CH$_3$)$_2$ | 107 |
| I.04 | CH | O | 3-Cl | CH(CH$_3$)$_2$ | 1.4(6H); 3.7(3H); 3.85 (3H); 5.35(1H); 5.5(2H) |
| I.05 | N | O | H | CH$_3$ | 65–72 |
| I.06 |  | O | H | CH$_2$CH$_3$ | 72–75 |

TABLE I-continued

I (structure shown: phenyl ring with $R^1_n$ substituent, $CH_2O$ linker to pyrimidine bearing $CF_3$ and $OR$; with $C=U-OCH_3$ and $O=C-V-CH_3$ side group)

| No. | U | V | $R^1_n$ | R | Phys. data [M.p. (° C.), IR (cm$^{-1}$), $^1$H-NMR (ppm)] |
|---|---|---|---|---|---|
| I.07 | N | O | H | CH(CH$_3$)$_2$ | 84–88 |
| I.08 | N | O | 3-Cl | CH(CH$_3$)$_2$ | 106–108 |
| I.09 | N | NH | H | CH$_2$CH$_3$ | 88–90 |
| I.10 | N | NH | H | CH(CH$_3$)$_2$ | 86–88 |
| I.11 | N | NH | 3-Cl | CH(CH$_3$)$_2$ | 116–118 |

Examples of the action against animal pests

It was possible to show the action of the compounds of the general formula I against animal pests by the following experiments:

The active compounds were prepared
a) as a 0.1% strength solution in acetone or
b) as a 10% strength emulsion in a mixture of 70% by weight of cyclohexanone, 20% by weight of Nekanil® LN (Lutensol® AP6, wetting agent having emulsifier and dispersant action based on ethoxylated alkylphenols) and 10% by weight of Emulphor® EL (Emulan® EL, emulsifier based on ethoxylated fatty alcohols)

and appropriately diluted to the desired concentration with acetone in the case of a) or with water in the case of b).

After conclusion of the experiments, the lowest concentration in each case was determined at which the compounds still produced an 80–100% inhibition or mortality in comparison with untreated control experiments (action threshold or minimal concentration).

*Tetranychus telarius* (red spider mite), contact action

Heavily infested potted dwarf beans which showed the second pair of adult leaves were treated with aqueous active compound preparation. After 5 days in the greenhouse, the control success was determined by means of a binocular microscope.

In this test, the compounds I.01–I.07 and I.09–I.11 showed action thresholds from 2 to 400 ppm.

*Nephotettix cincticeps* (green rice leafhopper), contact action

Round filters were treated with the aqueous active compound preparation and then occupied with 5 adult leafhoppers. After 24 h, the mortality was assessed.

In this test, the compounds I.07 and I.08 showed action thresholds of 0.4 mg.

Examples of the action against harmful fungi

It was possible to show the fungicidal action of the compounds of the general formula I by the following experiments:

The active compounds were prepared as a 20% strength emulsion in a mixture of 70% by weight of cyclohexanone, 20% by weight of Nekanil® LN (Lutensol® AP6, wetting agent having emulsifier and dispersant action based on ethoxylated alkylphenols) and 10% by weight of Emulphor® EL (Emulan® EL, emulsifier based on ethoxylated fatty alcohols) and diluted with water according to the concentration desired.

The comparison compound used was active compound A (Example No. 25, Table I of EP-A 407 872).

Action against *Plasmopara viticola* (Vine Peronospora)

Potted vines (variety: Muller Thurgau) were sprayed with the active compound preparation until dripping wet. After 8 days, the plants were sprayed with a zoospore suspension of the fungus *Plasmopara viticola* and kept at 20–30° C. for 5 days at high atmospheric humidity. Before assessment, the plants were then kept for 16 h at high atmospheric humidity. Assessment was carried out visually.

In this test, the plants treated with 250 ppm of the compounds I.01–I.07, I.10 and I.11 according to the invention showed an attack of 5% or less while the plants treated with the same amount of the known active compound A were attacked to 25%. The untreated (control) plants were attacked to 75%.

Action against *Pyricularia oryzae* (Rice blast)

Rice seedlings (variety: Tai Nong 67) were sprayed with the active compound preparation until dripping wet. After 24 hours, the plants were sprayed with an aqueous spore suspension of the fungus *Pyricularia oryzae* and kept at 22–24° C. for 6 days at a relative atmospheric humidity of 95–99%. Assessment was carried out visually.

In this test, the plants treated with 250 ppm of the compounds I.01, I.02, I.04, I.06–I.08, I.10 and I.11 according to the invention showed an attack of 25% or less while the plants treated with the same amount of the known active compound A were attacked to 60%. The untreated (control) plants were attacked to 85%.

We claim:

1. A 2-[(2-alkoxy-6-trifluoromethylpyrimidin-4-yl) oxymethylene]phenylacetic acid of the formula I

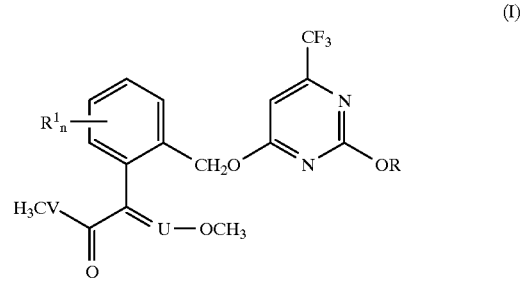

(I)

where the index and the substituents have the following meanings:
U is CH or N;
V is O or NH;
R is C$_1$–C$_6$-alkyl;
R$^1$ is cyano, halogen, C$_1$–C$_4$-alkyl, C$_1$–C$_4$-haloalkyl, C$_1$–C$_4$-alkoxy, C$_1$–C$_4$-haloalkoxy or phenyl;
n is 0 or an integer from 1 to 4, where the radicals R$^1$ may be different if the value of n is greater than 1.

2. The phenylacetic acid of the formula I defined in claim 1, where U is CH and V is O.

3. The phenylacetic acid of the formula I defined in claim 1, where U is N and V is O.

4. The phenylacetic acid of the formula I defined in claim 1, where U is N and V is NH.

5. The phenylacetic acid of the formula I defined in claim 1, where R is methyl, ethyl, or iso-propyl.

6. The phenylacetic acid of the formula I defined in claim 5, where U is CH and V is O.

7. The phenylacetic acid of the formula I defined in claim 5, where U is N and V is O.

8. A composition suitable for controlling animal pests and harmful fungi, which comprises a solid or liquid carrier and a phenylacetic acid of the formula I as defined in claim 1.

9. A method for controlling animal pests and harmful fungi, which comprises treating the pests or harmful fungi or the materials, plants, soil or seed to be protected from them with an effective amount of a phenylacetic acid of the formula I as defined in claim 1.

10. A composition suitable for controlling animal pests and harmful fungi, which comprises a solid or liquid carrier and a phenylacetic acid of the formula I as defined in claim 5.

11. A method for controlling animal pests and harmful fungi, which comprises treating the pests or harmful fungi or the materials, plants, soil or seed to be protected from them with an effective amount of a phenylacetic acid of the formula I as defined in claim 5.

12. A sulfone of the formula IV

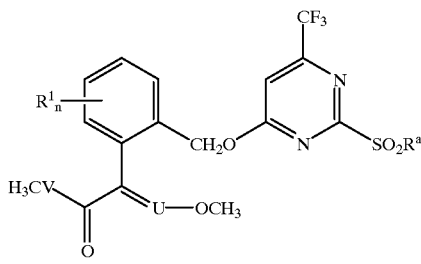
(IV)

where the index and the substituents have the following meanings:
U is CH or N:
V is O or NH:
$R^a$ is $C_1$–$C_4$-alkyl;
$R^1$ is cyano, halogen, $C_1$–$C_4$-alkyl, $C_1$–$C_4$-haloalkyl, $C_1$–$C_4$-alkoxy, $C_1$–$C_4$-haloalkoxy or phenyl:
n is 0 or an integer from 1 to 4, where the radicals $R^1$ may be different if the value of n is greater than 1.

13. A process for preparing the phenylacetic acid of the formula I defined in claim 1, which comprises reacting a pyrimidin-4-ol of the formula II

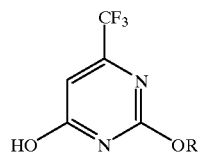
(II)

in an inert solvent in the presence of a base with a benzyl compound of the formula III

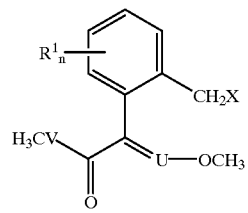
(III)

where X is a nucleophilically replaceable leaving group.

* * * * *